(12) United States Patent
Smith

(10) Patent No.: US 7,185,378 B2
(45) Date of Patent: Mar. 6, 2007

(54) ADJUSTABLE PAD/PLIABLE FLEXIBLE SUPPORT

(76) Inventor: Nathaniel Smith, 46 Front St., Holliston, MA (US) 01746

( * ) Notice: Subject to any disclaimer, the term of this patent is extended or adjusted under 35 U.S.C. 154(b) by 380 days.

(21) Appl. No.: 10/429,396

(22) Filed: May 5, 2003

(65) Prior Publication Data

US 2004/0039316 A1 Feb. 26, 2004

Related U.S. Application Data

(60) Provisional application No. 60/405,814, filed on Aug. 26, 2002.

(51) Int. Cl.
*A47G 9/00* (2006.01)
(52) U.S. Cl. .................. 5/642; 5/636; 5/640; 5/630; 16/444; 16/114.1; 16/422; 297/393; 297/284.5; 128/DIG. 23
(58) Field of Classification Search .................. 5/636, 5/655, 637, 639, 640, 642, 646, 648, 630, 5/632; 16/444, 114.1, 422; 397/393, 284.5; 128/DIG. 23
See application file for complete search history.

(56) References Cited

U.S. PATENT DOCUMENTS

| 4,243,026 A | 1/1981 | Barber |
| 4,790,042 A * | 12/1988 | Reich ............................. 5/655 |
| 5,371,909 A * | 12/1994 | McCarty ........................ 5/655 |
| 5,572,757 A * | 11/1996 | O'Sullivan ..................... 5/636 |
| 5,699,988 A * | 12/1997 | Boettger et al. ......... 248/122.1 |
| 6,238,358 B1 | 5/2001 | Philot et al. |
| 6,449,788 B1 * | 9/2002 | Nichols ........................ 5/636 |
| 6,457,195 B1 | 10/2002 | Holste |
| 6,658,681 B2 * | 12/2003 | Britto et al. ................... 5/655 |
| 6,698,044 B2 * | 3/2004 | Greenfield et al. ............ 5/624 |

FOREIGN PATENT DOCUMENTS

| DE | 4237792 A1 * | 5/1993 |
| WO | WO99/03432 | 1/1999 |

* cited by examiner

*Primary Examiner*—Alexander Grosz
(74) *Attorney, Agent, or Firm*—Wolf Greenfield & Sacks

(57) ABSTRACT

An adjustable support/pad that retains any shape to which it is configured and which may be reshaped to serve another purpose. The support/pad has at least one pliable coil spring in the shape of a flexible tube capable of being bent into multiple positions and holding any of the positions until it is again bent. The coil spring is embedded in a deformable cushion to provide comfort of the body wherever the support/pad is applied. The adjustable support can be made into a neck supporting pillow, or a cushion adapted to be removably attached to the back of a chair, to support the back of a seated user.

20 Claims, 17 Drawing Sheets

FIG.4
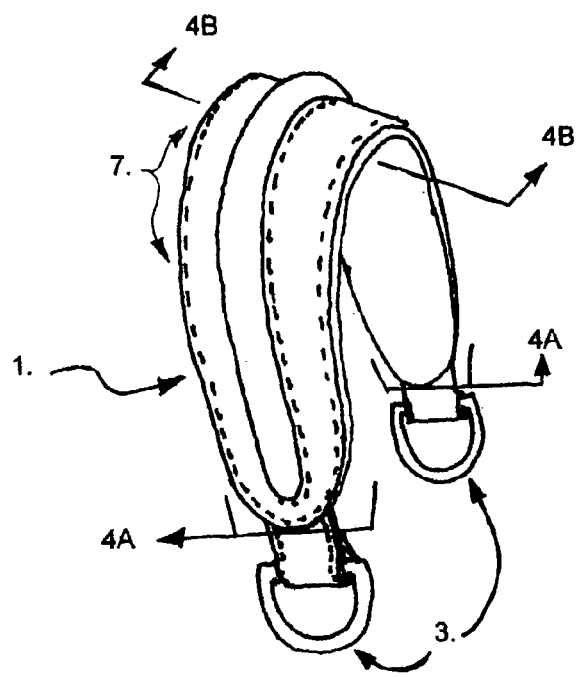
FIG.4A
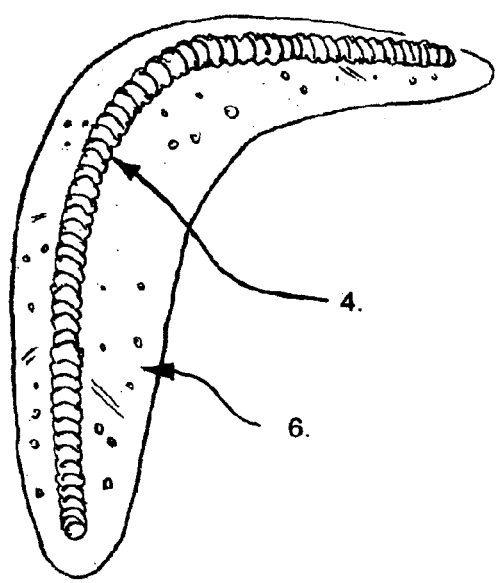
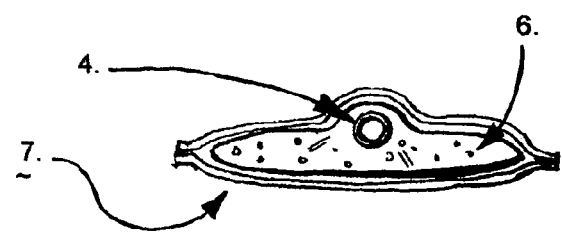
FIG.4B

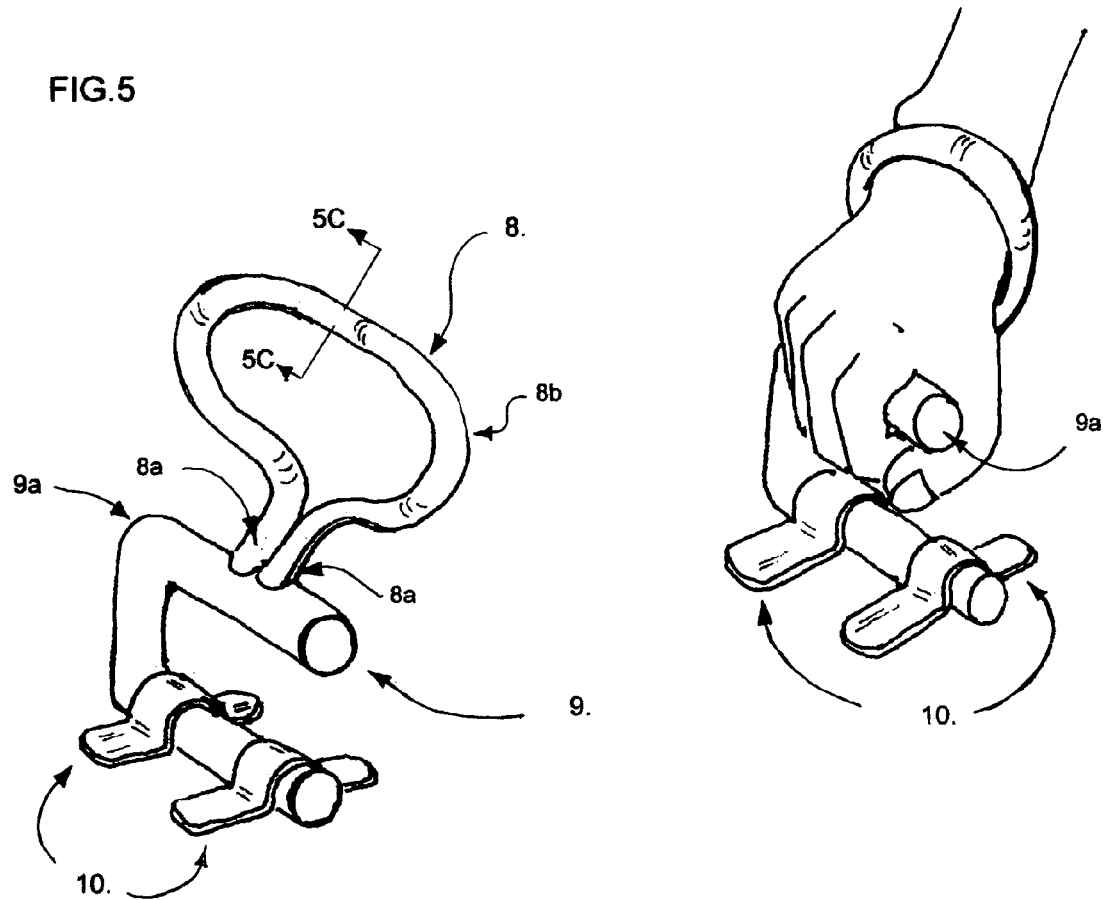

FIG.7D
FIG.7E
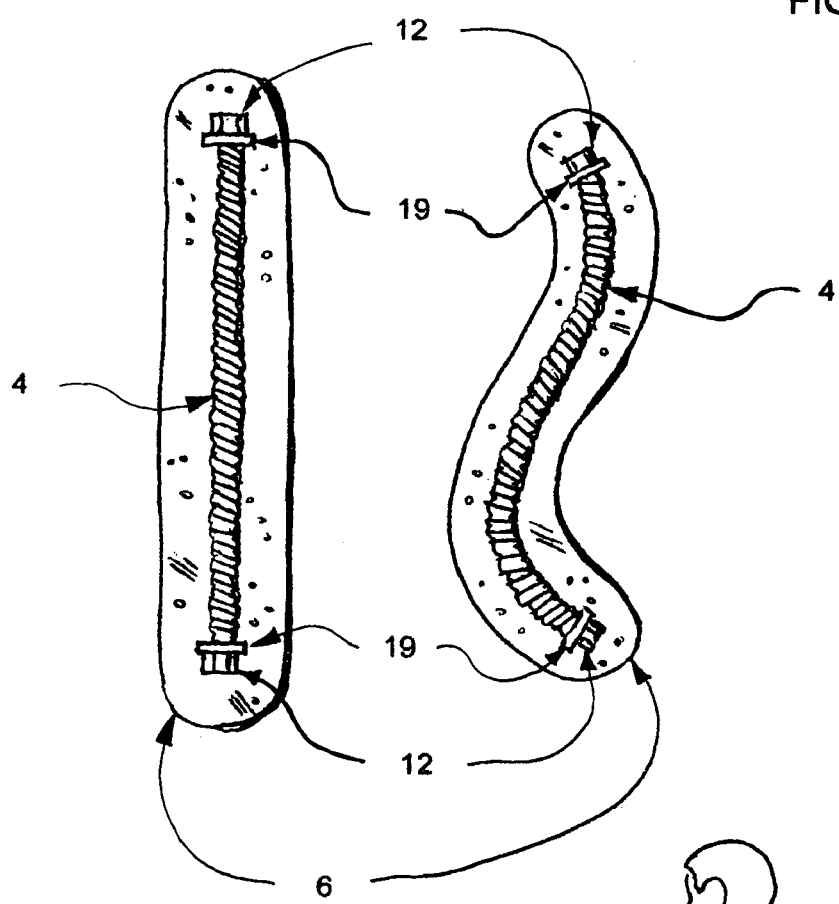
FIG.7F
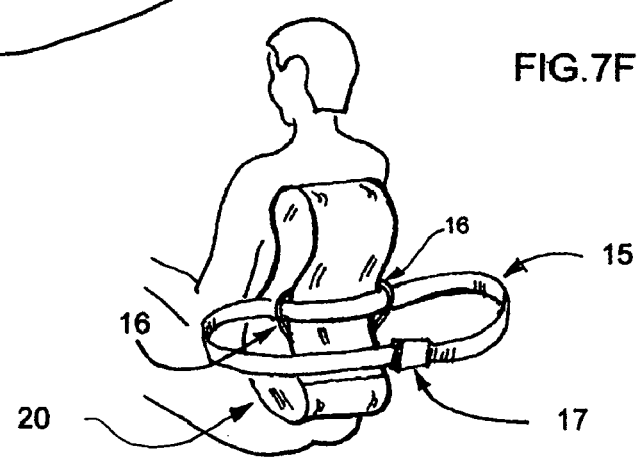

ADJUSTABLE PAD/PLIABLE FLEXIBLE SUPPORT

RELATED APPLICATIONS

This application is related to and claims the benefit of the filing date of U.S. Provisional Application No. 60/405,814, filed Aug. 26, 2002. U.S. Provisional Application No. 60/405,814 is hereby incorporated by reference in its entirety.

BRIEF DESCRIPTIONS OF THE INVENTION

The invention comprises the combination of one or more pliable coil springs, each formed into a flexible tubing, as might be found on an adjustable microphone neck or an adjustable lamp arm, encapsulated in a pad of soft elastically deformable material, such as polyurethane foam, or visco-elastic polyurethane, so that the spring(s) are completely covered and hidden from sight. The coil spring is often referred to as gooseneck wire and can be bent in multiple directions and into multiple positions, and because of its construction it will hold that position until reconfigured. There are many diameters and strengths of these pliable coil springs available and the size and length of this material can be selected to perform different tasks. These pliable coil springs may be made of metal, with a variety of coatings or be manufactured entirely of plastic. (One manufacturer of this type of flexible tubing is Uniprise International Incorporated located in Terryville, Conn.)

The elastically deformable cushion will provide the comfort, overall shape and added support when the invention is in use. A cover made of cotton, a synthetic, leather or any other suitable material may be provided for the pad to create an aesthetically pleasing finished look. In some cases the cover may be removable for washing, replacement or care.

BACKGROUND OF THE INVENTION

There are several types of supportive devises on the market today. Each is designed for a specific use and provides a degree of support to the user. All have either none or limited adjustability and adaptability to the individual user. In some of these devices, when an adjustment is made to fit an individual or particular application, the device can not be reconfigured, for use by others and/or for different applications.

The adaptability of the present invention makes it more comfortable and efficient than the prior devices, and it can be reconfigured, (flexed or straightened), for storage or travel.

BRIEF DESCRIPTION OF DRAWINGS

FIG. 3A is a cross-sectional view similar to FIG. 3 but showing the pad in a bent configuration;

FIG. 4 is a perspective view of an alternative embodiment of a shoulder strap embodying the invention;

FIGS. 4A and 4B are cross-sectional views of the pad of the embodiment shown in FIG. 4, taken along section lines 4A—4A and 4B—4B in that figure;

FIG. 5 is a perspective view of yet another application of the present invention embodied as part of a carrying handle;

FIG. 5A is a perspective view of the embodiment shown in FIG. 5, in use;

FIGS. 7D and 7E are cross-sectional views of yet another embodiment of the invention intended for use as a back support and showing the support in a straight and curved configuration, respectively;

FIG. 7F is a rear perspective view of the embodiments of FIGS. 7–7e employed as a back cushion and disposed in the shape of FIG. 7E;

DESCRIPTION OF THE PREFERRED EMBODIMENTS

Figure 1:
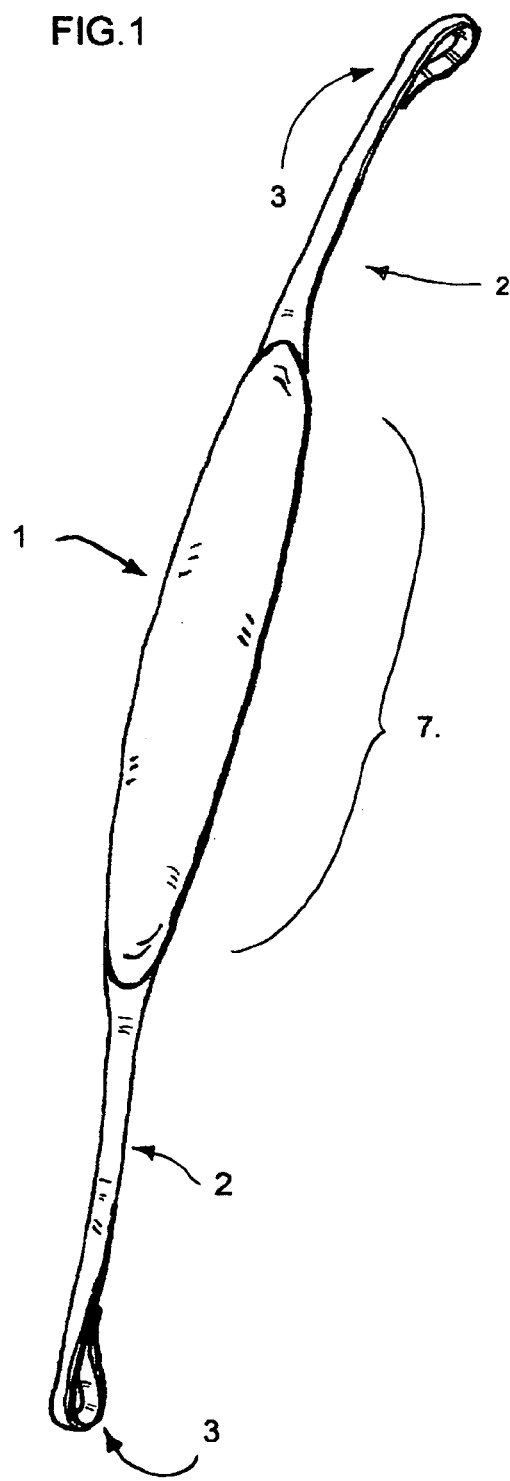
FIG. 1 is a perspective view of one embodiment of this invention configured as a shoulder strap and shown in a substantially flat plane.
Figure 2:
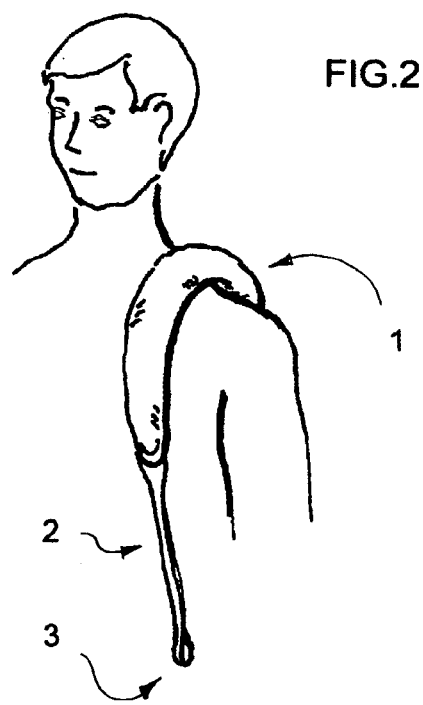
FIG. 2 is a perspective view of the embodiment shown in FIG. 1 and illustrated as it may be applied in use.
Figure 3:
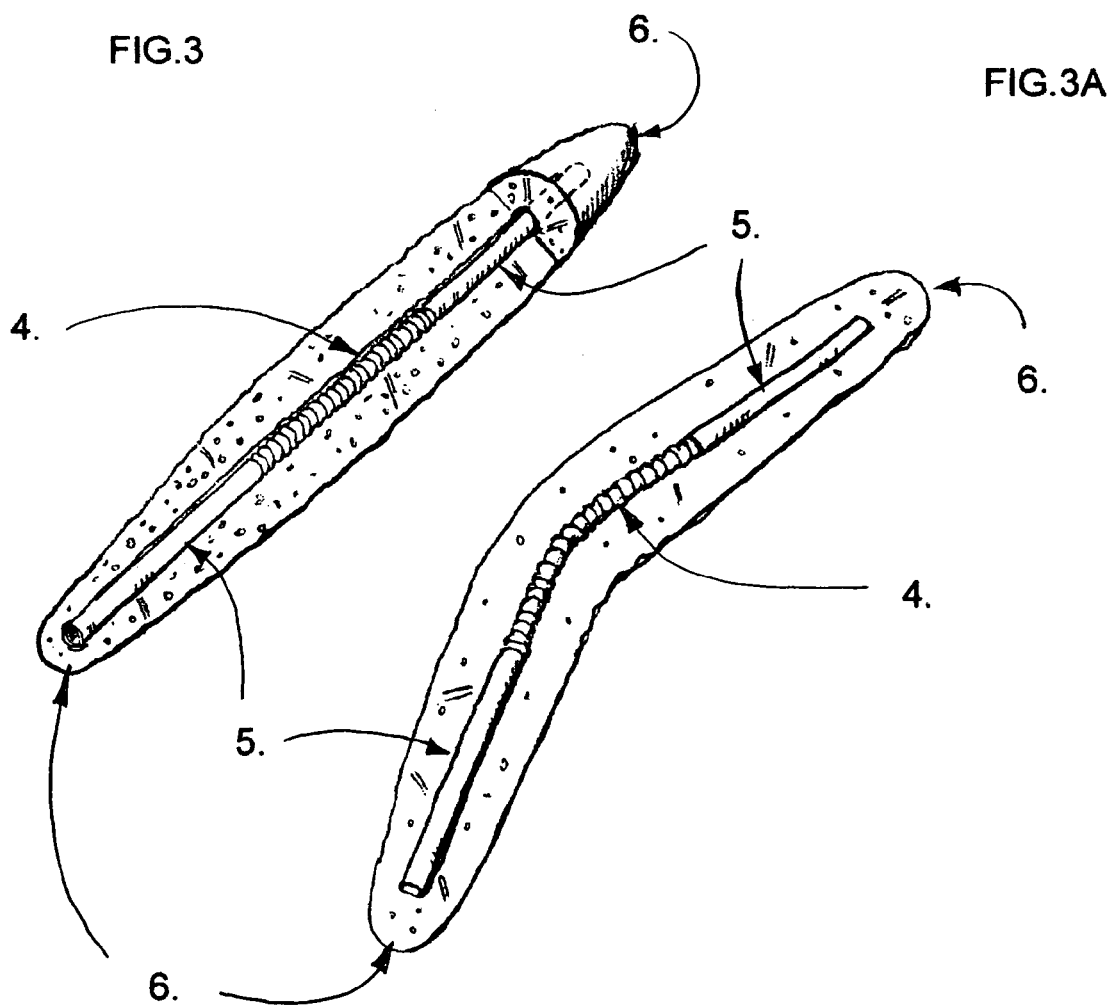
FIG. 3 is a cross-sectional view of the pad forming part of the embodiment of FIG. 1 and taken along section line 3—3 in FIG. 1.

The embodiment of the invention shown in FIGS. 1, 2, 3 and 3A is particularly suitable for use as a shoulder support for a brief case, luggage, hand bag or other generally similar article that is carried about on the shoulder of its user. The embodiment includes a pad 1 that carries a pair of straps 2, one at each end. The straps 2 may be separately formed and stitched or otherwise secured to the ends of the pad 1 or may comprise a single piece secured to the surface or interior of the pad with its ends extending beyond the ends of the pad. As shown in FIG. 3, the pad 1 includes a pliable coil spring 4 embedded in a cushioned material, and the spring may or may not include a pair of rigid sections 5 at one or both ends that may be made of solid or tubular material such as steel. While the rigid sections 5 are not pliable and are not intended to bend in any fashion to conform the shape of the pad to any special surface, the pliable coil spring 4 can be bent in multiple directions and into multiple positions, and the spring will hold the configuration in which it is placed until a force is applied to reconfigure it. It should be appreciated that if the rigid sections 5 are not employed, the pliable coil spring preferably extends adjacent to the ends 6 of the pad. In the preferred form, the pliable spring is made of metal and may be provided with a coating for different purposes. This type of coil often referred to as a gooseneck wire is easily bent in any direction and may define an acute or large angle or may have different curvatures in different sections. While metal is preferred, the wire may also be made of other materials such as plastic, as is known in the art. The pad cushion typically may be made of an elastically deformable material such as polyurethane foam or viscoelastic polyurethane that completely covers the spring as well as the rigid extensions 5 thereof if employed. A pad so constructed may readily be conformed to the surface configuration of the shoulder or other body part upon which the unit is to be placed when employed to carry a hand bag, briefcase, luggage, etc. When bent to a particular configuration, it will remain in that configuration until it is purposefully reconfigured. That is, the configuration of the pad embodying the spring is not prebiased to a particular shape.

The pad 1 may have a cover 7 perhaps bearing an aesthetically pleasing design or other indicia. The cover preferably is removable so that it may be cleaned or replaced. Typically, the cover may be made of leather, or a fabric of woven synthetic or natural fibers. The straps 2 may also be made of leather or other material possessing sufficient strength to bear the load applied to them. In the embodiment shown in FIGS. 1 and 2, the free ends of the straps are provided with loops 3 to attach the straps to the luggage, briefcase, carrying bag, etc. While loops are shown, it is to be understood that any suitable fasteners such as a buckles, snaps, rings etc. may be employed for that purpose.

It will be appreciated that the pliability of the pad enables it to be shaped so as to conform with the shoulder or other surface on which it is to be used. The pliability of the pad enhances comfort and weight distribution by maximizing the contact area between the pad and the shoulder. This feature also will assist in preventing the strap from slipping off the shoulder.

The rigid members 5 may be straight or may be preformed into curves to suit the particular application for the shoulder support. The rigid pieces may be connected to the ends of the spring or may telescope into the spring ends or if tubular, may receive the ends of the spring.

The embodiment shown in FIG. 4 also is intended for use as a shoulder strap and differs from that of FIGS. 1–3 in the configuration of the cushion, encapsulated spring and the fasteners disposed at the strap ends for connection to the hand bag, briefcase, luggage, etc. In this embodiment, the fasteners 3[1] are D-rings permanently attached to the ends of the strap 2. In FIG. 4B, the coil spring 4 is shown offset from the center of the cushion. The particular location of the spring with respect to the cushion will be determined by the particular application for the strap. For example, if the strap is intended to be used for carrying a heavy load, the cushion may be thicker on the concave or bottom sides of the spring in the curved configuration shown in FIGS. 4A and 4B.

Figure 5B:
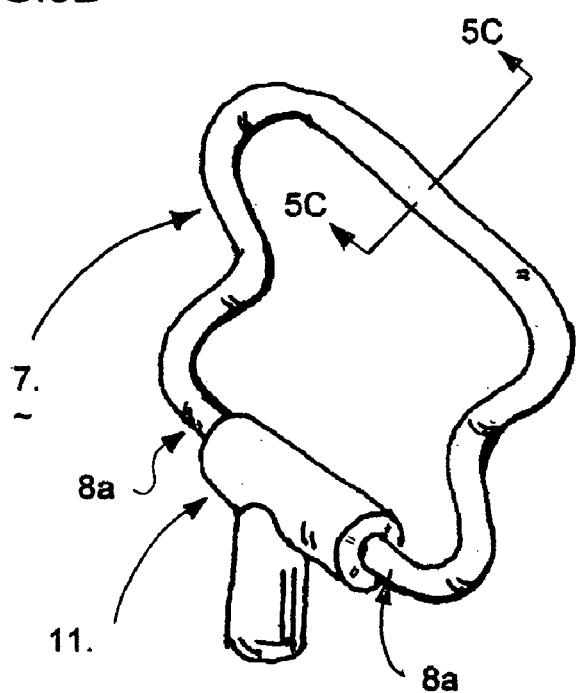
FIG. 5B is a perspective view of yet another application of the present invention incorporated into a carrying handle.
Figure 5C:
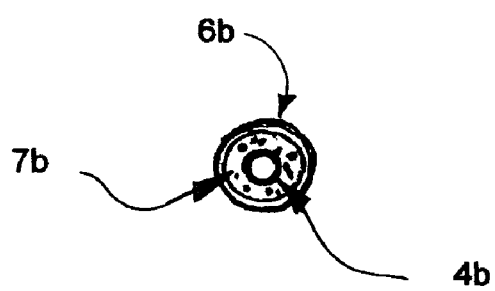
FIG. 5C is a cross-sectional view taken along the section lines 5C—5C in both FIGS. 5 and 5B.

FIG. 5 illustrates the invention embodied in an ergonomic handle assembly. The handle assembly shown includes a U-shaped handle that typically may be made of metal and that normally would be attached to the luggage or other heavy load by brackets 10 fastened to the upper surface of the luggage. The upper arm 9 of the handle which serves as the grip employs yet another embodiment of the present invention comprised of a cushion encapsulated flexible coil spring (see FIG. 5C). The cushion encapsulated spring 8 serves as a wrist band whose ends 8a are attached to the grip 9a of the handle 9. Typically, the band 8 may be circular in cross-section and the gooseneck wire may extend essentially throughout the full length of the band and may include non-pliable (rigid) end sections similar to those shown in FIG. 3 to make the connection between the band and the grip 9a. In use, the band extends about and conforms to the shape of the wrist of the user as suggested in FIG. 5A. The coil spring within the band allows it to bend into a complex shape and conform to the wrist so as to distribute the weight of the load carried by the handle 9 onto the wrist and to securely attach the handle with its load to the person carrying it. The end portions 8a of the band are disposed within the palm of the user's hand, and the elastically deformable cushion covering is comfortable when the hand engages the handle. This handle assembly is particularly helpful when the user is required to carry another object with his/her other hand.

FIG. 5B illustrates yet another embodiment of the invention including gooseneck wire, cushion and cover incorporated into a rigid handle assembly. In this embodiment, the ends 8a of the strap are attached to the ends of the grip 11 rather than to its midsection as shown in the embodiment of FIG. 5. The band defines a closed loop with the grip 11 that enables the band to extend about the wrist of the carrier in a fashion somewhat similar to that of the embodiment shown in FIGS. 5 and 5A.

FIG. 5C is a cross-sectional view typical of the cross-section of the bands used in both embodiments of FIGS. 5 and 5B. The spring 4b is shown encapsulated in the cushion 7b that in turn is enclosed in the cover 6b. The cover 6b typically may be made of leather or some other sturdy material which is aesthetically appealing, wears well and comfortable.

Figure 6:
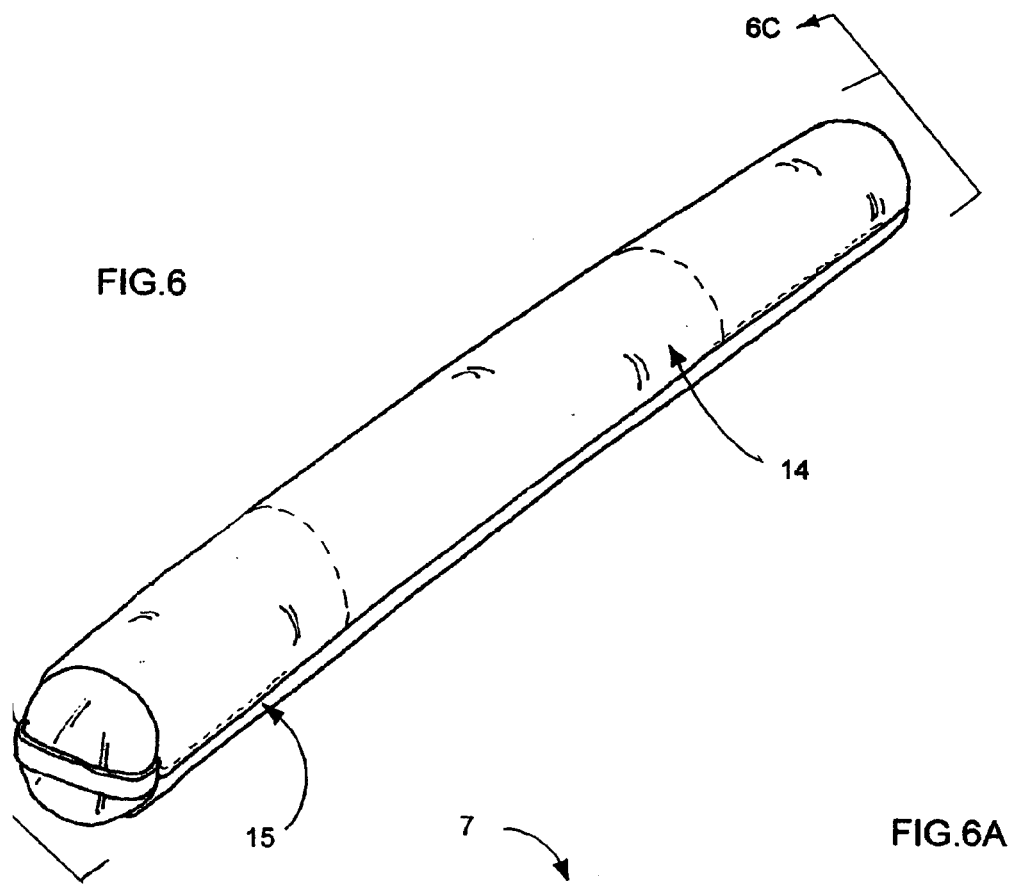
FIG. 6 is a perspective view of yet another application of the invention embodied in a neck support and shown in a straight configuration.
Figure 6A:
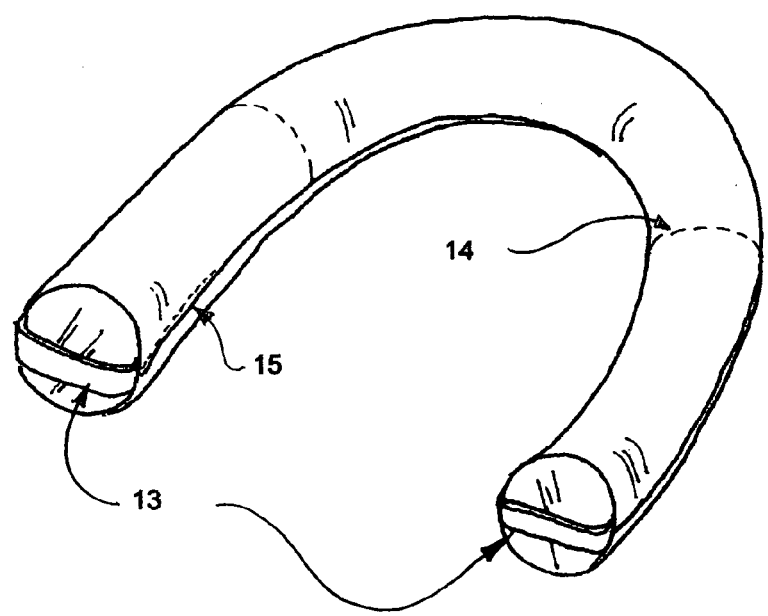
FIG. 6A is a perspective view of the neck support shown in FIG. 6 but bent into a U-shape so as to surround the sides and back of a user's neck.
Figure 6B:
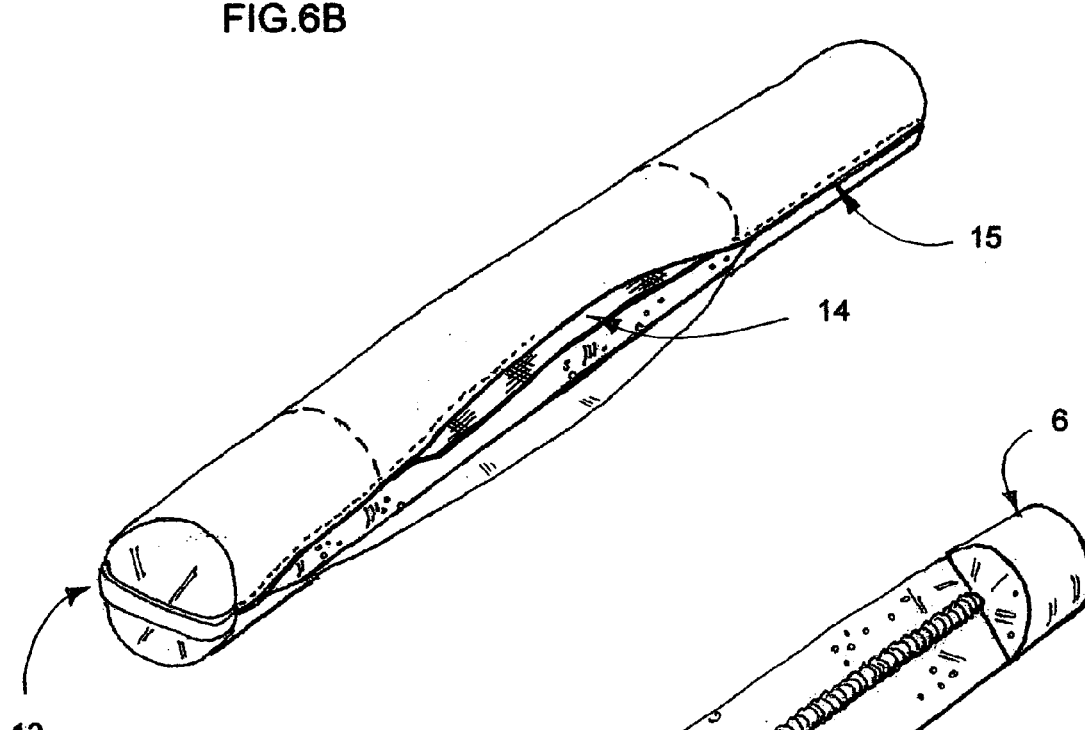
FIG. 6B is a perspective view of yet another embodiment of a neck brace, shown in a straight configuration.
Figure 6C:
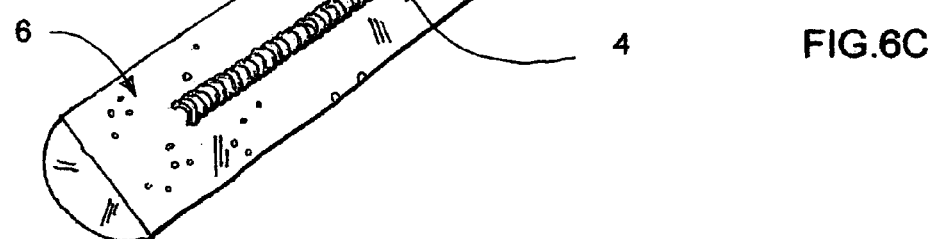
FIG. 6C is a cross-sectional view of the embodiment of neck support shown in FIG. 6 and taken along section line 6C—6C in FIG. 6.
Figure 6D:
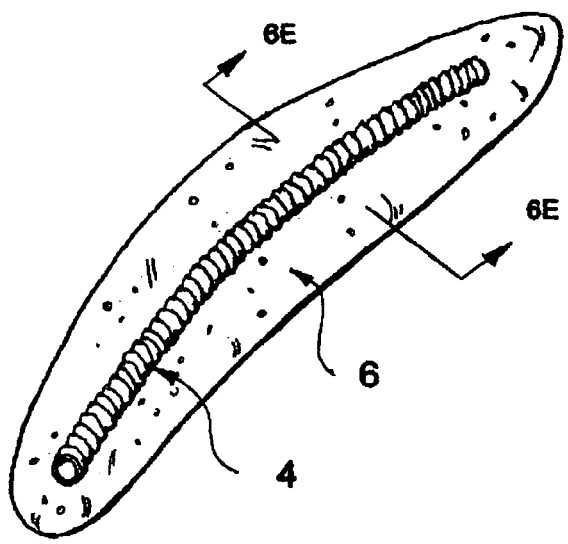
FIG. 6D is a perspective view of yet another embodiment of neck brace shown on the neck of a user.
Figure 6F:
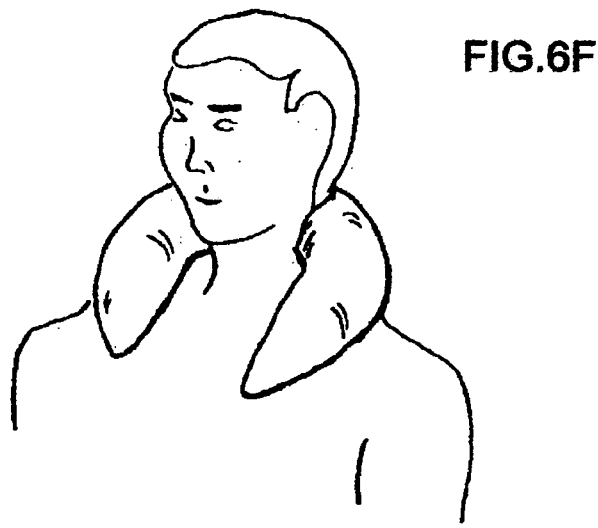
FIG. 6E is a cross-sectional view of the neck brace taken along section line 6E—6E of FIG. 6D.
Figure 6E:
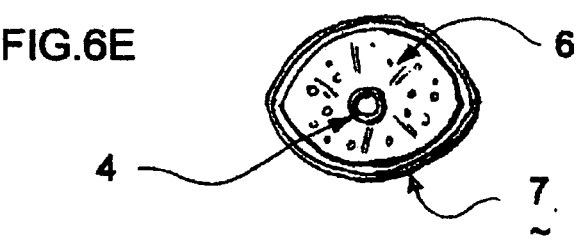

In FIGS. 6 through 6E, several embodiments of this invention are shown, particularly intended for use as a neck support. In the embodiment of FIGS. 6 and 6A, the neck support is shown embodied in an elongated cylindrical cushion shown in a straight configuration in FIG. 6 and a bent or functional configuration in FIG. 6A. The cushion shown is of a constant circular cross-section, and a gooseneck type coil spring is embedded in it, having the same characteristics as shown in the previously described embodiments. The coil spring may have rigid end portions as taught in FIG. 3 if the extent of the pliable section is to be limited. This configuration is particularly designed to provide back and side support for the neck. The cushion may be made of materials suggested above in connection with the other embodiments and while a uniform circular cross-section is shown, the cross-sectional shape may vary both in size as well as shape for specific applications. Moreover, while in the embodiment of FIGS. 6 and 6A, the ends are shown to be flat, they may be rounded or have any other desirable configuration, again dictated by the particular application. In the embodiment shown, handles 13 are provided on the ends of the cushion to facilitate the application of the neck support to the neck of the person using it. The handles may assist not only in the mounting of the neck support on the body of the user, but may facilitate shaping of the unit to its desired configuration. This embodiment, like the others, may include a cover that preferably is detachable. The cover may contain pockets that typically may be used to carry heating packs, cold packs or any other desirable material that may advantageously be used together with the neck support. The neck support shown in FIG. 6B includes a pocket 14 to receive any beneficial substance. The cover may also carry aesthetically pleasing designs as well as any other indicia. In FIGS. 6 and 6A the longitudinally extending line on the surface may represent either a seam or a zipper, depending upon the particular construction employed for the cover.

The neck support shown in FIGS. 6D and 6E differs from that of FIGS. 6 and 6B in the configuration of the elastically deformable cushion. This shaped neck support is particularly applicable when principal support is required for the back of the neck and/or if the user has a relatively short neck. In this embodiment, the cushion is shown to be elliptically shaped both in longitudinal and transverse cross-section, but it is to be understood that the particular cross-section of the cushion is not limited. As in the other embodiments, the cushion encapsulates the pliable coil spring, and the cushion may be enclosed in a fixed or removable cover.

Figure 7:
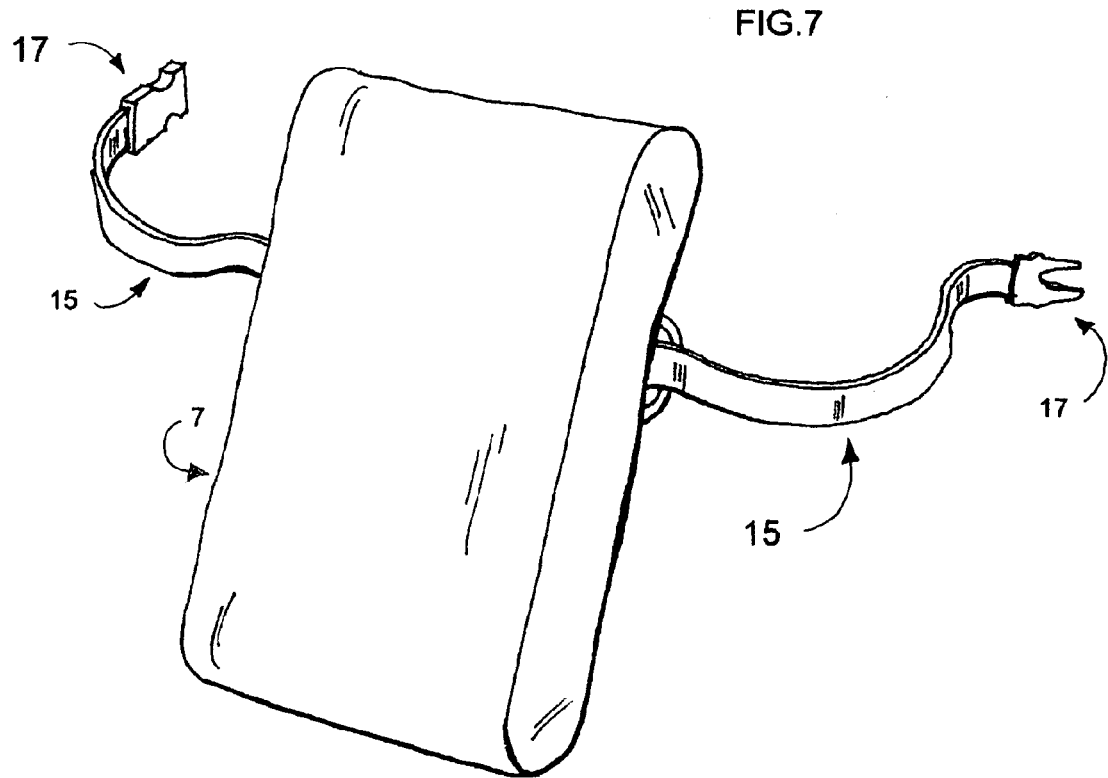
FIGS. 7 and 7A are front and back perspective views of still another application of the present invention embodied in a back support.

In FIGS. 7 to 7F, the invention is shown embodied in an adjustable back support that may be reconfigured to fit any individual. The device may be of varying shapes and sizes, but typically would be made in a rectangular configuration, roughly the width of an average person's back. But as suggested, it could be made in varying sizes, for example, small, medium and large, so as to best perform its function for people of different stature. Moreover, while the device shown is of generally uniform thickness, the back support may vary in thickness from one part to another. For example, the portion of the cushion intended to provide lumbar support may be thicker than the upper portion of the cushion.

FIGS. 7B to 7E are cross-sectional views of the back support. The support is shown to include a pair of gooseneck wires 4 at the top end of which are rigid extensions 5. The combination of spring 4 and extension 5 extends substantially the whole height of the cushion. The two are shown to be generally parallel to one another and are rigidly spaced apart both at their top and bottom by rigid connecting plates 19 that typically may be made of steel. The ends of each spring/extension 4, 5 are secured to the plates 19. In the cross-sectional views of FIGS. 7D and 7E, rigid extensions 5 are omitted, but rather both ends of the gooseneck wires are connected to the plates 19.

Figure 7A:
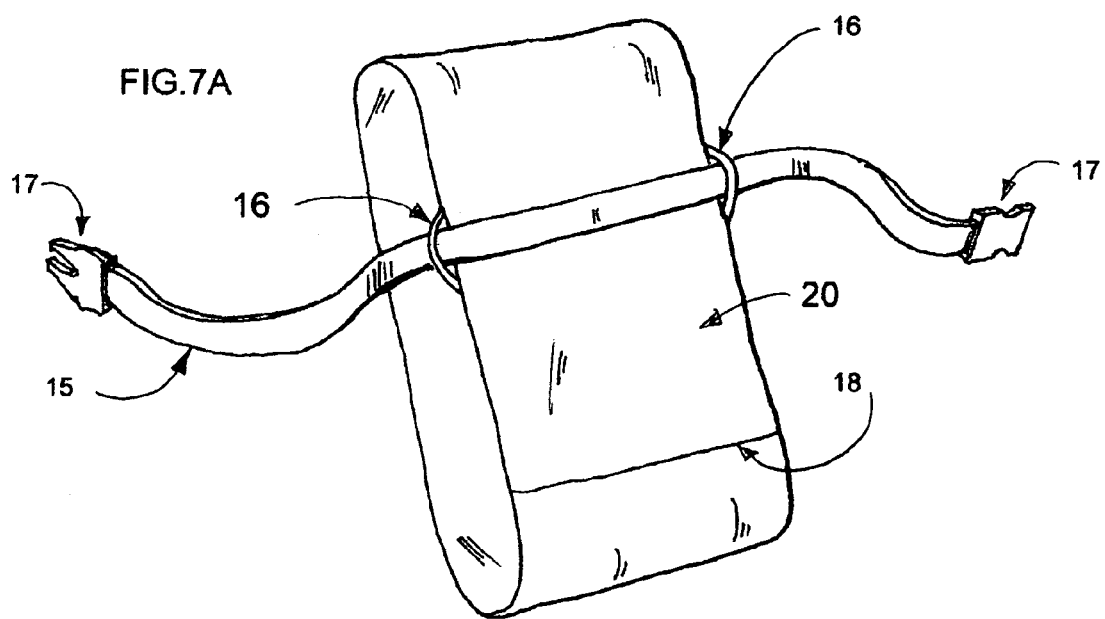
Figure 7B:
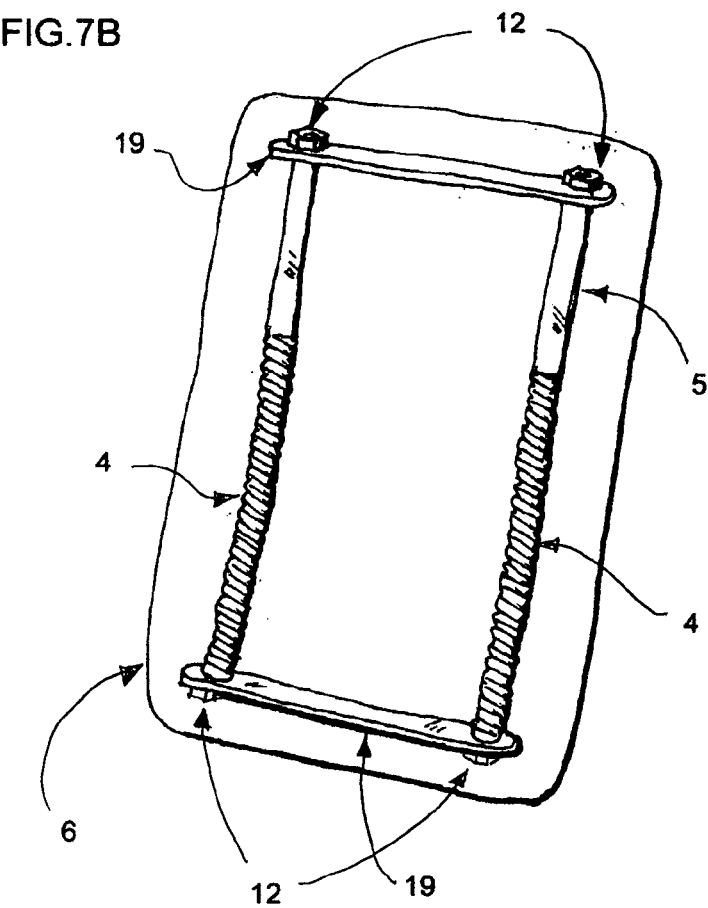
FIG. 7B is a cross-sectional view of the cushion of the back support taken on a plane parallel to the front and rear surfaces of the support.

In FIGS. 7 and 7A a belt 15 is shown slidably attached to the cushion by means of a pair of loops 16. The belt enables the support to be attached to the back of a chair, automobile seat, etc., and the belt preferably is adjustable and is provided with a snap buckle or other form of attachment to facilitate mounting the support in place. The use of the cushion as a back support on a chair is suggested in FIG. 7F. As shown in the back view of FIG. 7A, the support is provided with a cover 20 with a flap-type opening as shown at 18 so as to enable the cushion to be slipped in and out of the cover. As in the other embodiments of the invention, the cover may be made of a wide variety of materials and may be decorated in any fashion.

Figure 7C:
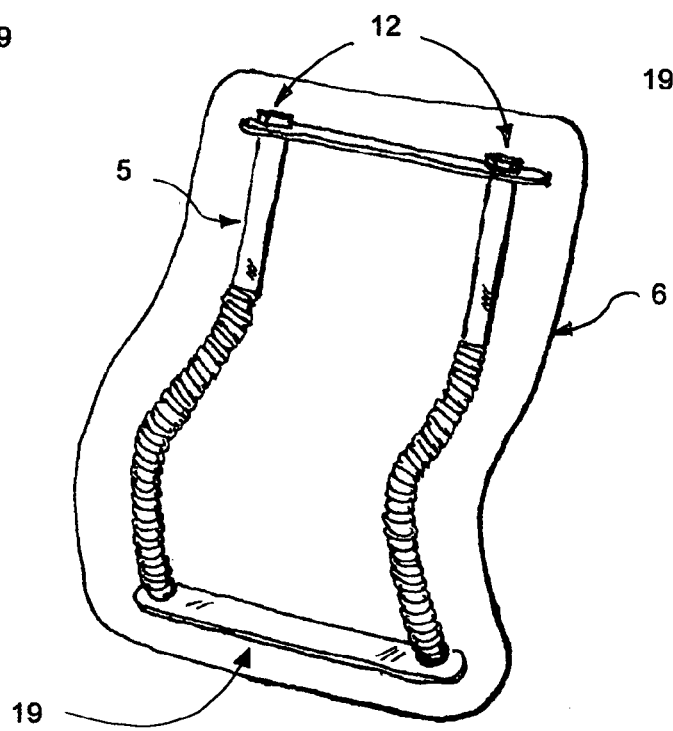
FIG. 7C is a cross-sectional view similar to FIG. 7B, but showing the back support in a modified configuration for use.

The two pliable springs 4 embedded in the deformable cushion and that operate in tandem allow the device to be wider as is needed for a back support as compared to a shoulder support or neck support. While two such springs are shown in the embodiment illustrated, the back support may employ more than two springs if required for special applications. The added number of springs will cause the support to retain its configuration and a greater force will be required to alter it. This is desirable as greater force is required to support the weight of the user's back than in other of the applications of the invention. Preferably, the ends of the springs with or without the rigid extensions, the plates 19 and their connections to the springs cause the springs to work in tandem and inhibit the support from being manipulated three-dimensionally, that is, the two springs work in unison and make it unlikely that the unit will become asymmetrical. In FIG. 7C the two pliable coil springs have been manipulated so as to create a support for the lumbar region of the user's lower back as is further shown in FIG. 7F.

The embodiment of the invention shown in FIGS. 7D and 7E does not employ the rigid extensions and in FIG. 7E, the support is shown in an S configuration to provide support to the lower back and lumbar region.

Figure 8:
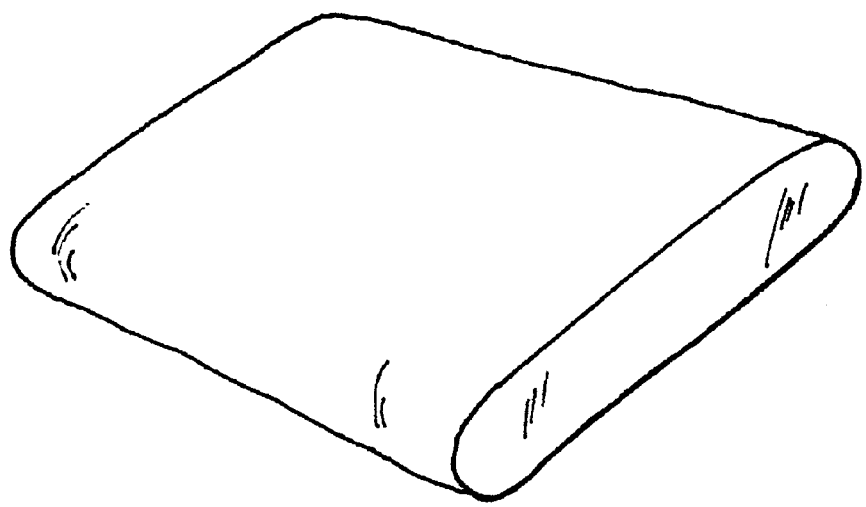
FIG. 8 is a perspective view of yet another application of the invention embodied in a pillow.
Figure 8A:
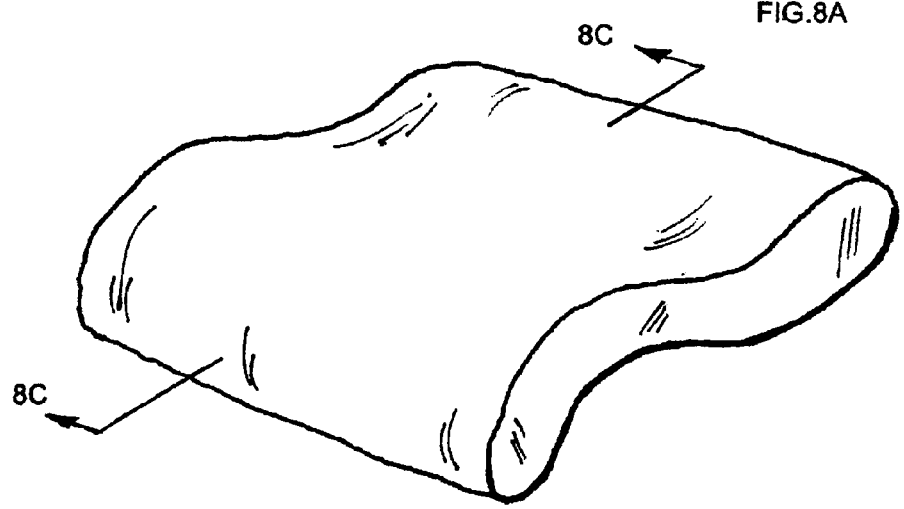
FIG. 8A is a perspective view of the pillow shown in FIG. 8 but in a different configuration.
Figure 8B:
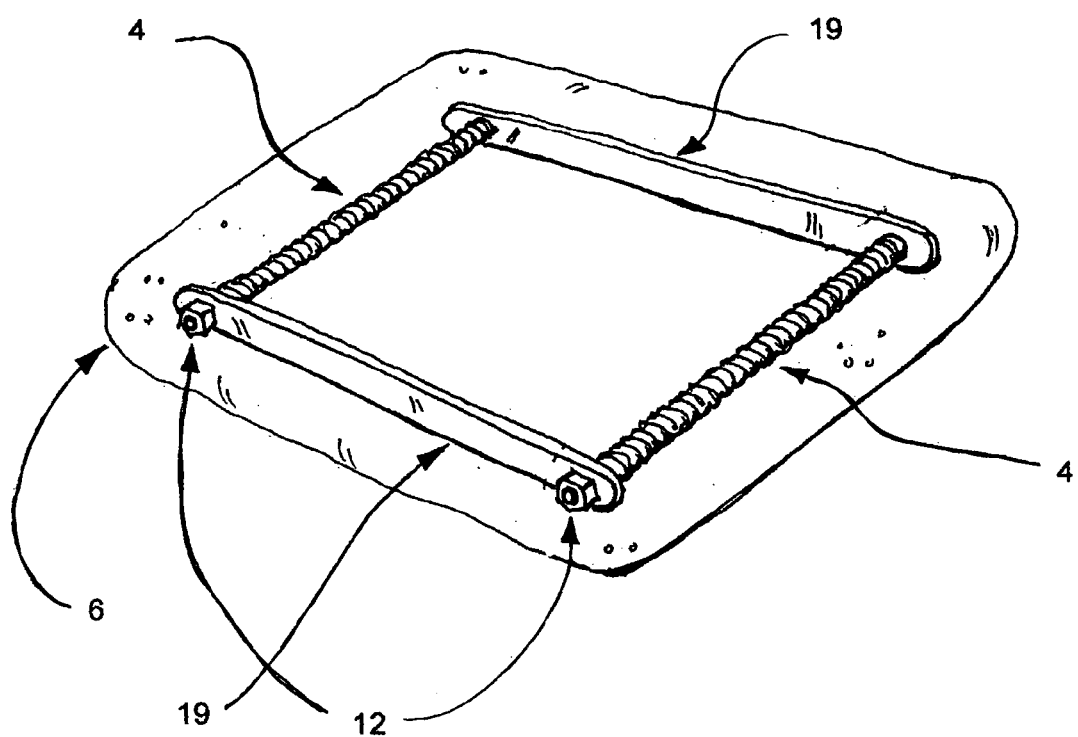
FIG. 8B is a perspective view showing the interior of the pillow of FIGS. 8 and 8A.
Figure 8C:
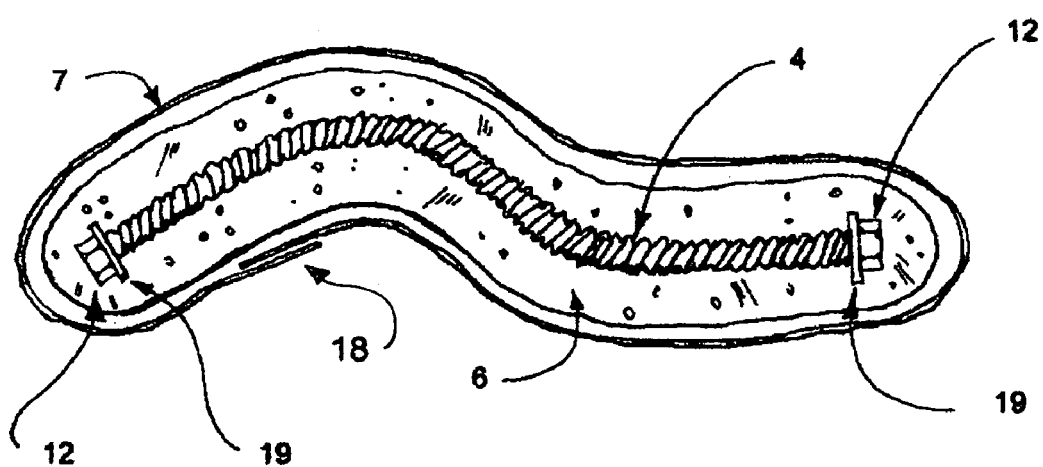
FIG. 8C is a cross-sectional view of the pillow taken along section line 8C—8C in FIG. 8A.
Figure 8D:
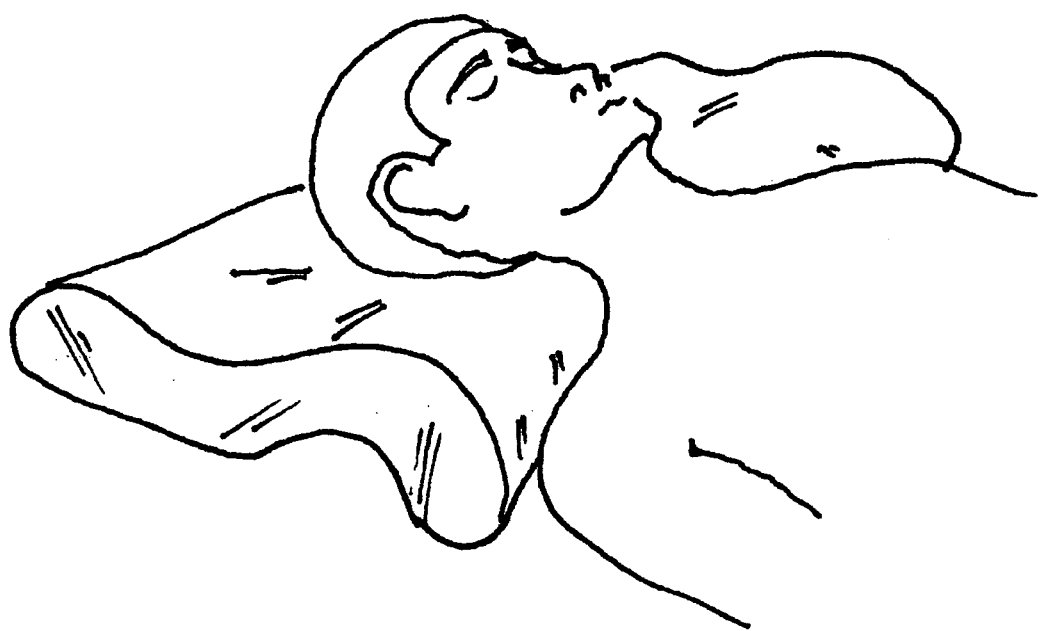
FIG. 8D is a perspective view showing the pillow of FIGS. 8–8c in use.
Figure 9:
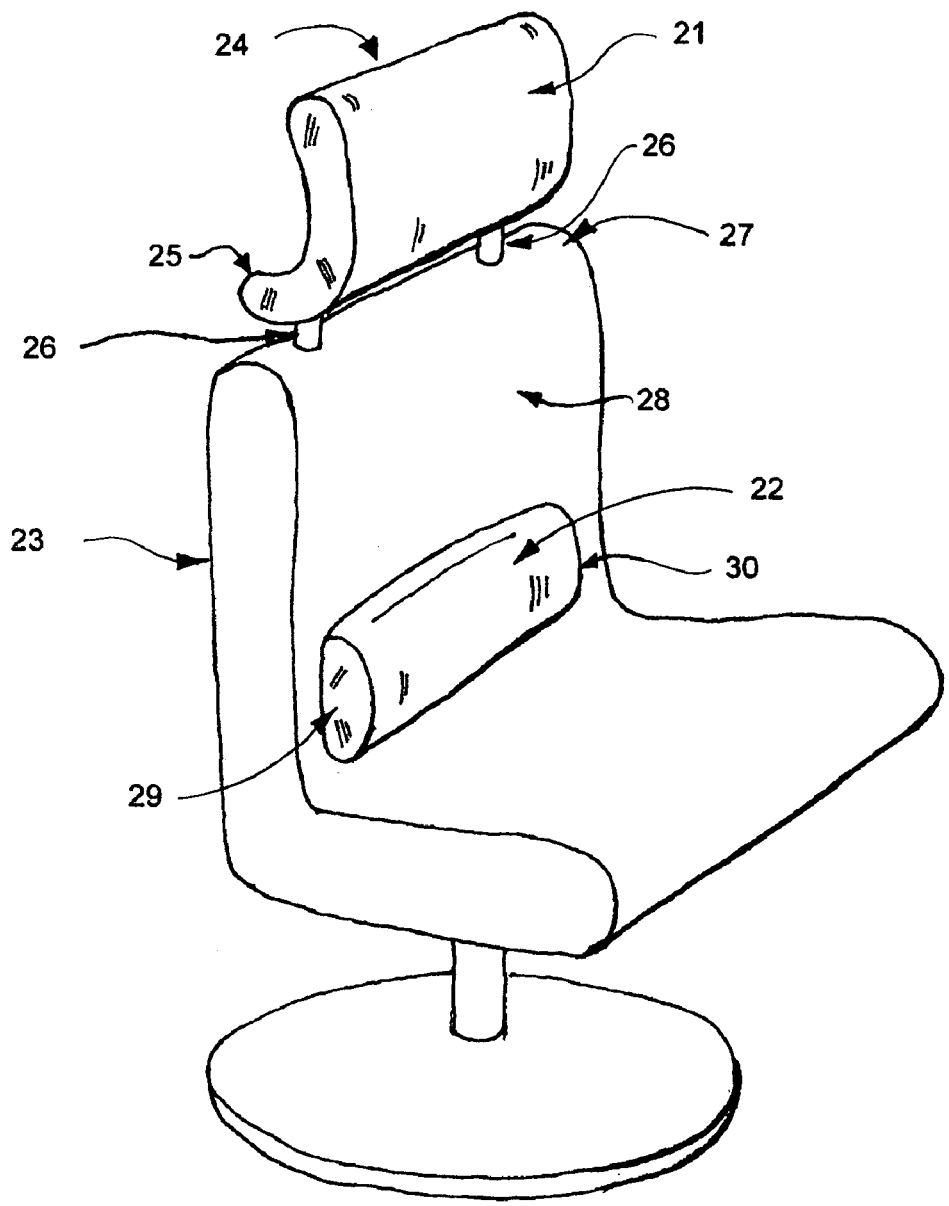
FIGS. 9 and 9A are perspective views of a chair utilizing two embodiments of the present invention utilized as a headrest and lumbar back support and in two different configurations.
Figure 9A:
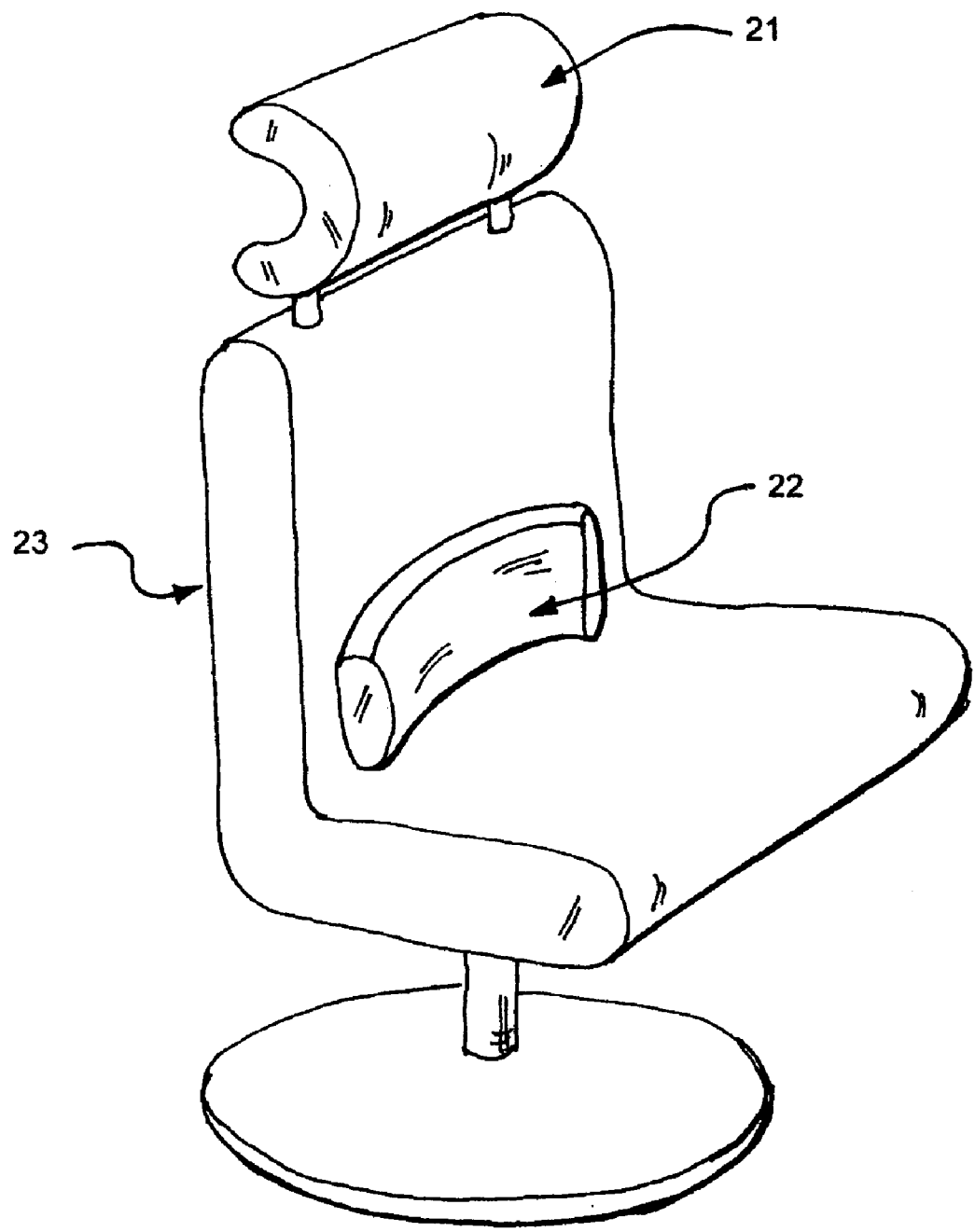

FIG. 8D shows the support configured for use as an adjustable pillow, and its construction is very similar to that of the embodiments shown in FIGS. 7 through 7F with the omission of the belt 16. Like the earlier embodiment, the support includes two gooseneck wires connected in tandem by plates 19 just as in the earlier embodiment. The springs and plates are embedded in a deformable cushion as in the other embodiments, and the cushion is enclosed in a case that preferably is removable by means of the flap 18 also previously described. In use, the pillow may be bent as shown for example, in FIG. 8D to support the head as well as the neck of the user. In FIGS. 9 and 9A additional embodiments of the support are illustrated. In FIG. 9, two supports 21 and 22 are shown mounted on a chair 23 which represents either an easy chair, office chair, automobile seat or any other chair. Support 21 is a pliable, flexible headrest that would include at least two gooseneck wires extending between the top and bottom edges 24 and 25 in a generally vertical direction. The cushion as illustrated in FIG. 9 is shown supported on a pair of posts 26 secured to the top edge 27 of the backrest 28 of the chair. As in the embodiments of FIGS. 7 and 8, the multiple gooseneck wires are connected by rigid plates that promote a parallel relationship for the wires. The head support 21 is shown in two different positions in FIGS. 9 and 9A. In FIG. 9A the headrest is generally in a C-shaped configuration while in FIG. 9 the headrest support is adjusted to a J-shape.

The support 22 shown in FIGS. 9 and 9A is also adjustable so as to provide a variable lumbar support. One or two pliable springs are provided in the lumbar support 22 and extend horizontally between the ends 29 and 30 of the support. In the embodiment of FIG. 9 the support is mounted essentially flat against the chair back while in the embodiment of FIG. 9A, the support is shown to be in a gently curved configuration. The support 22 may either be built into the chair or may simply be attached to it by a strap, Velcro, or other fasteners well known in the art. It should be understood that the headrest and lumbar support 21 and 22 are constructed like the other embodiments shown, that is, they comprise a flexible and pliable gooseneck type wire embedded in a deformable cushion that in turn may have a separate and preferably removable cover.

Each of the embodiments provides a pliable and flexible support, each having its own shape and function best suited for its intended purpose. The pliable and reconfigurable shoulder support can adjust to fit each user and will stay in position on the shoulder for comfort and weight distribution as will all of the applications shown. The shape of the cushion when conformed to the shape of the shoulder, helps distribute the weight of the object carried by the support. Maximizing weight distribution is an important advantage of the invention.

The ergonomic handle assembly may readily be used for a briefcase or a bag, a walking cane or for some other purpose. Because it wraps around the wrist of the user, it provides means for lifting the case, bag, etc. and also serves to distribute the weight across the hand and wrist. The user may readily manipulate the shape of the handle assembly so as to precisely fit his/her wrist.

The neck support may be of uniform cross-section throughout its length or may diminish in cross-sectional size from end-to-end. In either case, it may be bent to provide comfort and adjustable support for the user's head and neck whenever and wherever the user wishes. The device can be reconfigured for new positions of use or for different applications.

As a lumbar and back support, the pad may advantageously be rectangular or wedge-shaped and include two or more pliable coil springs coupled together for added support and strength. Coupling the pliable coils together by means of the rigid plate shown in the embodiments illustrated allows the user to bend the back support into position across the lower back and lumbar region.

The adjustable pillow embodying the present invention may also be shaped to provide the user with individualized comfort. The pillow typically may be rectangular or wedge-shaped and may be of uniform or variable thickness. Like the back support, the adjustable pillow preferably has two or more gooseneck wires coupled together for added support and strength.

Finally, it should be appreciated that the present invention may be used in conjunction with other products, such as office seating, automotive and airline seating, recliners, hand bags and luggage, bed pillows, etc. so as to make them adjustable and ergonomically supportive. There are many applications for the invention.

In any of the embodiments of the invention, pockets may be provided in the cover or in the cushion material for holding such aids as hot or cold packs, etc. This feature is specifically shown in FIG. 6B but may be incorporated into all embodiments of the invention.

Those skilled in the art will appreciate that numerous modifications may be made of this invention without departing from its spirit. Therefore, the invention is not to be limited to one or more of the specific embodiments illustrated and described. Rather, the scope of the invention should be determined by the appended claims and their equivalents.

The invention claimed is:

1. An adjustable support for engaging and supporting a portion of the surface of the body of a user and that will retain any shape to which it is configured and which may be repeatedly reshaped to serve in another comprising,
   at least one pliable coil spring in the shape of a flexible tube capable of being bent into multiple curved positions and holding any of said positions until it is again bent,
   and a deformable cushion encapsulating and following the configuration of the coil spring in whatever curvature it is bent and conforming to the shape of a portion of the body of the user.

2. An adjustable support as described in claim 1 wherein a cover encloses the cushion.

3. An adjustable support as described in claim 2 wherein the cover is removable.

4. An adjustable supported as described in claim 1 wherein the cushion is sized to encircle the sides and back of the neck of a person to serve as a neck brace.

5. An adjustable support as described in claim 1 wherein the support/pad has a pair of spaced apart pliable coil springs which extend through a substantial portion of the deformable cushion adjacent opposed marginal edges thereof.

6. An adjustable support as described in claim 5 wherein the deformable cushion forms a rectangular pad and the coil springs are substantially parallel to one another.

7. An adjustable support as described in claim 6 wherein the ends of the coil springs are joined together by a rigid member encapsulated within the cushion.

8. An adjustable support as described in claim 7 wherein the cushion is generally rectangular and the springs extend generally parallel to opposite sides of the cushion.

9. An adjustable support as described in claim 8 wherein a strap is attached to the cushion for encircling the backrest of a chair with the springs extending generally in a vertical direction enabling the support/pad to function as a backrest on a chair.

10. An adjustable neck pillow that is pliable and retains any shape to which it is configured and which may be reshaped to serve another purpose comprising
    at least one gooseneck wire capable of being bent into multiple positions and holding any of said positions until it is again bent,
    and a deformable cushion material encapsulating the wire in whatever position the wire is bent to lie comfortably against the neck of the user.

11. An adjustable neck pillow as described in claim 10 wherein the gooseneck is a pliable metal coil spring.

12. An adjustable neck pillow as described in claim 11 wherein the gooseneck wire includes a plurality of pliable coil springs.

13. An adjustable neck pillow as described in claim 10 wherein the deformable material is polyurethane.

14. An adjustable neck pillow as described in claim 10 wherein the deformable material includes polyurethane.

15. The adjustable neck pillow as described in claim 10 wherein the cushion is cylindrical in shape.

16. The adjustable neck pillow as described in claim 15 wherein the gooseneck wire is disposed generally parallel to the axis of the cushion.

17. The adjustable neck pillow as described in claim 10 wherein a removable cover encloses the cushion.

18. The adjustable neck pillow as described in claim 10 wherein the cushion is elliptically-shaped in transverse cross-section.

19. The adjustable neck pillow as described in claim 18 wherein the cushion is elliptically-shaped in longitudinal cross-section.

20. The adjustable neck pillow as described in claim 17 wherein pockets are formed in the cover.

\* \* \* \* \*